United States Patent [19]

Lee

[11] Patent Number: 4,774,027

[45] Date of Patent: Sep. 27, 1988

[54] PROCESS FOR THE PREPARATION OF N-L-AMINODICARBOXYLIC ACID ESTERS AND NEW COMPOSITIONS USED IN THE PREPARATION THEREOF

[75] Inventor: Thomas D. Lee, Scarsdale, N.Y.

[73] Assignee: General Foods Corporation, White Plains, N.Y.

[21] Appl. No.: 119,947

[22] Filed: Nov. 13, 1987

[51] Int. Cl.[4] ............................................. C07C 117/00
[52] U.S. Cl. ...................................... 260/349; 560/169
[58] Field of Search .......................................... 260/349

[56] References Cited

U.S. PATENT DOCUMENTS

| | | | |
|---|---|---|---|
| 2,286,169 | 6/1942 | Hechenbleikner | 260/349 X |
| 3,475,403 | 10/1969 | Mazur et al. | 560/39 |
| 3,532,741 | 10/1970 | Fukunaga | 260/349 X |
| 3,786,039 | 1/1974 | Ariyoshi et al. | 560/41 |
| 3,833,553 | 9/1974 | Ariyoshi et al. | 560/41 |
| 3,839,395 | 10/1974 | Otsuka et al. | 260/349 X |
| 3,879,372 | 4/1975 | Boesten | 560/41 X |
| 3,933,781 | 1/1976 | Bachman et al. | 560/41 X |

FOREIGN PATENT DOCUMENTS 0199257  10/1986  European Pat. Off. .

OTHER PUBLICATIONS

Pedrosa, et al.; C.A. 106:85001f (1987).

*Primary Examiner*—Joseph Paul Brust
*Attorney, Agent, or Firm*—Linn I. Grim; Thomas A. Marcoux; Daniel J. Donovan

[57] ABSTRACT

This present invention provides an improved method for producing N-L-aspartyl-D-alanine fenchyl ester or N-L-aspartyl-methylalanine fenchyl ester and new compositions of fenchol derivatives which are intermediate compositions in the preparation of the above described fenchyl esters.

9 Claims, No Drawings

PROCESS FOR THE PREPARATION OF N-L-AMINODICARBOXYLIC ACID ESTERS AND NEW COMPOSITIONS USED IN THE PREPARATION THEREOF

This invention describes a process for the production of N-L-aminodicarboxylic acid esters which are particularly well suited as sweeteners in edible foodstuffs. The process, as used, also utilizes new compositions as intermediates to provide the desired sweetening products.

In co-pending U.S. patent application Ser. Nos. 082,246 filed Aug. 5, 1987 and 898,063 filed Aug. 19, 1986 and European Patent Office patent application No. 0199257, published Oct. 29, 1986 all applications commonly assigned to the same assignee of the present application, there is described new sweeteners and the process for producing same. These sweeteners are N-L-Aminodicarboxylic acid esters and of particular significance are the fenchyl sweeteners known as N-L-aspartyl-D-alanine or N-L-aspartyl-methylalanine fenchyl esters which have outstanding sweetness properties. In the above described co-pending applications, there are several reaction schemes described to prepare the highly desirable fenchyl esters. In one reaction scheme, compounds of general formula I (protected α-aminodicarboxylic acid) and II (amino-ester compound) are condensed to form compounds of general formula III. Subsequent removal of protecting groups B and Z from compounds of general formula III give the desired compounds of general formula III (B=Z=H).

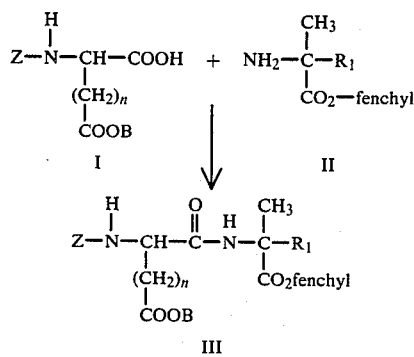

In these, group Z is an amino protecting group, B is a carboxyl protecting group and $R_1$ is a methyl or hydrogen group. A variety of protecting groups known in the art may be employed. Examples of many of these possible groups may be found in "Protective Groups in Organic Synthesis" by T. W. Green, John Wiley and Sons, 1981. Among the preferred groups that may be employed are benzyloxycarbonyl for Z and benzyl for B.

Coupling of compounds with general formula II to compounds having general formula III employs established techniques in peptide chemistry. One such technique uses dicyclohexylcarbodiimide (DCC) as the coupling agent. The DCC method may be employed with or without additives such as 4-dimethylaminopyridine, hydroxybenzotriazole or copper chloride. The DCC coupling reaction generally proceeds at room temperature, however, it may be carried out from about −20° to 50° C. in a variety of solvents inert to the reactants. Thus suitable solvents include, but are not limited to, N,N-dimethylformamide, methylene chloride, toluene and the like. Preferably, the reaction is carried out under an inert atmosphere such as argon or nitrogen. Coupling usually is complete within 2 hours but may take as long as 24 hours depending on reactants.

Various other methods can be employed to prepare the desired compounds. The following illustrates such methods using aspartic acid as the amino dicarboxylic acid.

For example, U.S. Pat. Nos. 3,786,039; 3,833,553; 3,879,372 and 3,933,781 disclose the reaction of N-protected aspartic anhydrides with amino acids and amino acid derivatives to yield the desired products. These N-protected aspartic anhydrides can be reacted with compounds of formula II by methods disclosed in the above patents. As described in U.S. Pat. No. 3,786,039 compounds of formula II can be reacted directly in inert organic solvents with L-aspartic anhydride having its amino group protected by a formyl, carbobenzyloxy, or p-methoxycarbobenzyloxy group which is subsequently removed after coupling to give compounds of general formula III (B=H). The N-acyl-L-aspartic anhydrides are prepared by reacting the corresponding acids wich acetic anhydride in amounts of 1.0–1.2 moles per mole of the N-acyl-L-aspartic acid at 0° to 60° C. in an inert solvent. The N-acyl-L-aspartic anhydrides are reacted with preferably 1 to 2 moles of compounds of formula II in an organic solvent capable of dissolving both and inert to the same. Suitable solvents are, but not limited to, ethyl acetate, methyl propionate, tetrahydrofuran, dioxane, ethyl ether, N,N-dimethylformamide and benzene. The reaction proceeds smoothly at 0° to 30° C. The N-acyl group is removed after coupling by catalytic hydrogenation with palladium on carbon or with HBr or HCl in a conventional manner. U.S. Pat. No. 3,879,372 discloses that this coupling method can also be performed in an aqueous solvent at a temperature of −10° to 50° C. and at a pH of 4–12.

Another method for the synthesis of the desired compounds is the reaction of compounds of formula II with suitable aspartic acid derivatives in which protecting groups have been attached to the amino and beta-carboxy groups and the alpha carboxy group has been converted to a reactive ester function. As disclosed in U.S. Pat. No. 3,475,403 these coupled products may be deprotected as described to yield the desired compounds.

An alternative scheme to the desired coupled compounds involves reaction of compounds of formula II with L-aspartic acid N-thiocarboxyanhydride by the method of Vinick and Jung, Tet, Lett., 23, 1315–18 (1982). An additional coupling method is described by T. Miyazawa, Tet. Lett., 25, 771 (1984).

Compounds of general formula II are synthesized using art recognized techniques. For example, compounds of formula II can be synthesized by standard esterification methods known in the art by reacting the free acid or acid functional equivalents, such as esters or anhydrides, with the corresponding alcohols under ester-forming conditions, as for example in the presence of mineral acids, such as hydrochloric or sulfuric acids, organic acids, such as p-toluenesulfonic acids or coupling agents such as dicyclohexylcarbodimide. Reaction temperatures are in the range of −78° to reflux. The reaction is carried out in a solvent that will dissolve both reactants and is inert to both as well. Solvents include, but are not limited to methylene chloride, diethyl ether, tetrahydrofuran, dimethylsulfoxide, N,N-dimethylformamide, and the like.

With regard to the removal of protecting groups from compounds of formula III and N-protected precursors of formula II, a number of deprotecting techniques are known in the art and can be utilized to advantage depending on the nature of the protecting groups. Among such techniques is catalytic hydrogenation utilizing palladium on carbon or transfer hydrogenation with 1,4-cyclohexadiene. Generally the reaction is carried out room temperature but may be conducted from 5° to 65° C. Usually the reaction is carried out in the presence of a suitable solvent which may include, but are not limited to water, methanol, ethanol, dioxane, tetrahydrofuran, acetic acid, t-butyl alcohol, isopropanol or mixtures thereof. The reaction is usually run at a positive hydrogen pressure of 50 psi but can be conducted over the range of 20 to 250 psi. Reactions are generally quantitative taking 1 to 24 hours for completion.

In any of the previous synthetic methods the desired products are preferred recovered from reaction mixtures by crystallization. Alternatively, normal or reverse-phase chromatography may be utilized as well as extraction or other means.

The reaction of (+) fenchol with $ClCH_2COCl$ and ultimately producing a fenchyl ester of N,N-dialkylamino acetic acid is described in the article "Synthesis and Structure of Fenchol Amine Esters" Raikova, T. S.; Voitekhovskaya, G. I. Valimae, T.; Udarov, G. B.; (Inst. Fiz-org, Khim, Minsk, USSR) Khim. Pri. Soedin, 1983, (3), 305–8. As a starting material, these compositions could not be used to produce the desired N-L-aspartyl D-alanine or methylalanine fenchyl ester sweeteners.

Although the above described processes are satisfactory for the production of N-L-Aminodicarboxylic Acid esters, another process has been discovered which significantly speeds up the reacton and is very suitable for large scale synthesis.

THE INVENTION

The process of this invention for producing N-L-aspartyl-DL-alanine or methylalanine fenchyl ester comprises the following steps:

Step (1)—reacting fenchol, in the presence of an organic base, with a compound represented by the formula:

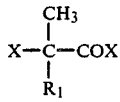

To produce the compound:

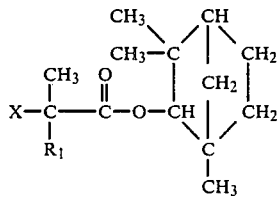

X is a chloro, bromo or iodo group and $R_1$, is a hydrogen or methyl group. The organic base used in this reaction includes, among others; triethylamine; N,N-diisopropylethylamine; dimethylaniline; 1,8-bis(dimethylamino)naphthalene; pyridine; 4-dimethylaminopyridine; 2,6-di-tert-butylpyridine; N-methylmorpholine and the like. The fenchol alcohol used herein includes $\alpha(+)$fenchol, $\alpha(-)$fenchol; $\beta(+)$fenchol and $\beta(-)$fenchol. The halogenated isobutyryl and propanoyl compounds used in this reaction includes; $\alpha$-chloropropanoyl chloride; $\alpha$-chloroisobutyryl chloride; $\alpha$-bromopropanoyl bromide; $\alpha$-bromoisobutyryl bromide; $\alpha$-iodopropanoyl iodide; and $\alpha$-iodoisobutyryl iodide. The reaction in the presence of solvents such as dichloromethane, ethylacetate, tetrahydrofuran, etc., takes place at temperatures in the range from about 0° C. to ambient temperature (room temperature) until the reaction is complete. The amounts of each of the reactants can range from about 0.05 to about 1.5 molar ratio, preferably from about 0.9 to about 1.1 molar ratio.

The compositions prepared in this step include, among others:

O-($\alpha$-chloropropanoyl)$\alpha(+)$fenchol;
O-($\alpha$-chloropropanoyl)$\alpha(-)$fenchol:
O-($\alpha$-chloropropanoyl)$\beta(+)$fenchol;
O-($\alpha$-chloropropanoyl)$\beta(-)$fenchol;
O-($\alpha$-bromopropanoyl)$\alpha(+)$fenchol;
O-($\alpha$-bromopropanoyl)$\alpha(-)$fenchol;
O-($\alpha$-bromopropanoyl)$\beta(+)$fenchol;
O-($\alpha$-bromopropanoyl)$\beta(-)$fenchol;
O-($\alpha$-iodopropanoyl)$\alpha(+)$fenchol;
O-($\alpha$-iodopropanoyl)$\alpha(-)$fenchol;
O-($\alpha$-iodopropanoyl)$\beta(+)$fenchol;
O-($\alpha$-iodopropanoyl)$\beta(-)$fenchol;
O-($\alpha$-chloroisobutyryl)$\alpha(+)$fenchol;
O-($\alpha$-chloroisobutyryl)$\alpha(-)$fenchol;
O-($\alpha$-chloroisobutyryl)$\beta(+)$fenchol;
O-($\alpha$-chloroisobutyryl)$\beta(-)$fenchol;
O-($\alpha$-bromoisobutyryl)$\alpha(+)$fenchol;
O-($\alpha$-bromoisobutyryl)$\alpha(-)$fenchol;
O-($\alpha$-bromoisobutyryl)$\beta(+)$fenchol;
O-($\alpha$-bromoisobutyryl)$\beta(-)$fenchol;
O-($\alpha$-iodoisobutyryl)$\alpha(+)$fenchol;
O-($\alpha$-iodoisobutyryl)$\alpha(-)$fenchol;
O-($\alpha$-iodoisobutyryl)$\beta(+)$fenchol;
O-($\alpha$-iodoisobutyryl)$\beta(-)$fenchol;

Step (2)—The product of the first step is reacted with sodium azide or aluminum azide to produce the following.

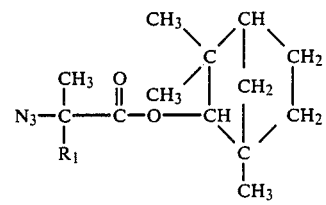

wherein $R_1$ is a methyl or hydrogen group. This reaction, in the presence of solvents such as N,N-dimethylformamide, acetonitrile, water and the like as well as mixed solvents, occurs at temperatures from about 25° C. to about 80° C., preferably about 35° C. to about 45° C. with vigorous stirring until no further reaction occurs. The amounts of reactants can range from about 0.05 to about 1.5 molar ratios. The new compositions of this step produced include:

O-($\alpha$-Azidoisobutyryl)$\beta(+)$fenchol;
O-($\alpha$-Azidoisobutyryl)$\beta(-)$fenchol;
O-($\alpha$-Azidoisobutyryl)$\alpha(+)$fenchol;

O-(α-Azidoisobutyryl)α(−)fenchol;
O-(α-Azidopropanoyl)β(+)fenchol;
O-(α-Azidopropanoyl)β(−)fenchol;
O-(α-Azidopropanoyl)α(+)fenchol; and
O-(α-Azidopropanoyl)α(−)fenchol Step (3)—The product of step 2 is hydrogenated in the presence of a known hydrogenation catalyst such as palladium on charcoal at room temperature to produce

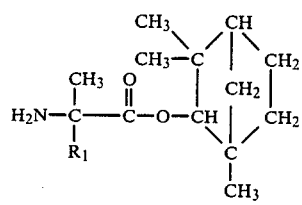

wherein $R_1$ is a methyl or hydrogen group.

Step (4)—The product of step 3 is reacted with a compound having the formula:

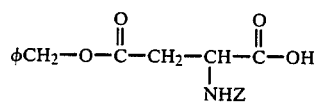

in the presence of a peptide coupling reagent to produce a compound having the formula:

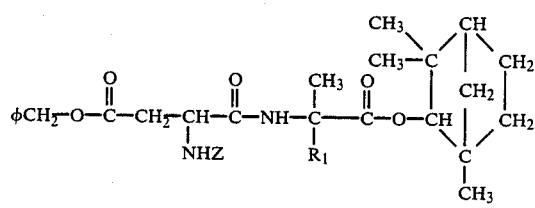

wherein Z is an amine protector and $R_1$ is a methyl or hydrogen group.

It is essential for this process that an amino protecting group is used in the reaction. A variety of protecting groups are known in the art and may be employed. Examples of many of these possible groups may be found in "Protective Groups in Organic Synthesis" by T. W. Green, John Wiley and Sons, 1981.

Coupling of compounds as carried out in this step employs established techniques used in peptide chemistry such as described in "The Peptides, Analysis, Synthesis, Biology; Vol. 1, Major Methods of Peptide Bond Formation," E. Gross and J. Meienhofer, Academic Press, Inc., 1979. Coupling agents such as carbonyldiimidazole or dicyclohexylcarbodiimide can be used. The coupling reaction generally proceeds at room temperature, however it may be carried out from about −20° C. to about 50° C. in a variety of solvents inert to the reactants. Suitable solvents include, among others: dichloromethane, N,N-dimethylformamide, toluene and the like. The coupling reaction usually is complete within 2 hours but may take as long as 48 hours depending on reactants. The amount of reactants are usually maintained at molar ratios from about 0.05 to about 1.5.

Step 5 is taking the coupled reaction product of step 4 and hydrogenating the coupled product to remove the amino protecting group at the same time, benzyl ester group is converted to carboxylic acid. This process, as well as the hydrogenation of step 3 can be carried out using catalytic hydrogenation utilizing palladium on carbon or a transfer hydrogenation technique. Generally, the reaction is carried out at room temperature but may be conducted from about 5° C. to about 65° C. Usually the reaction is carried out in the presence of a suitable solvent which may include, but are not limited to water, methanol, ethanol, dioxane, tetrahydrofuran, acetic acid, t-butyl alcohol, isopropanol or mixtures thereof. The reaction is usually run at a positive hydrogen pressure of about 50 psi but can be conducted over the range of about 20 to about 250 psi. Reactions are generally quantitative taking 1 to 24 hours for completion. In the cases where amino protecting groups (e.g. t-butyloxycarbonyl) cannot be removed by hydrogenation, the products of step 5 will have to be further treated with acid hydrolysis conditions. Generally, the reaction is carried out by a treatment with trifluoroacetic acid or hydrochloric acid, with or without solvent, from 0° C. to 50° C.

The products of the process of this invention are recovered and purified utilizing standard procedures. The products produced by this process include:
N-L-aspartyl-DL-alanine[β(+)fenchyl]ester;
N-L-aspartyl-DL-alanine[β(−)fenchyl]ester;
N-L-aspartyl-DL-alanine[α(+)fenchyl]ester;
N-L-aspartyl-DL-alanine[α(−)fenchyl]ester;
N-L-aspartyl-D-alanine[β(+)fenchyl]ester;
N-L-aspartyl-D-alanine[β(−)fenchyl]ester;
N-L-aspartyl-D-alanine[α(+)fenchyl]ester;
N-L-aspartyl-D-alanine[α(−)fenchyl]ester;
N-L-aspartylmethylalanine[β(+)fenchyl]ester;
N-L-aspartylmethylalanine[β(−)fenchyl]ester;
N-L-aspartylmethylalanine[α(+)fenchyl]ester;
N-L-aspartylmethylalanine[α(−)fenchyl]ester;

The following examples further illustrate the invention:

EXAMPLE 1

Production of O-(α-Bromoisobutyryl)-β(+)fenchol

A mixture of β(+)fenchol (14.7 g), α-bromoisobutyryl bromide (28.1 g) and triethylamine (17 ml) was stirred in dichloromethane from 0° C. to room temperature overnight. Afterward, it was washed with dilute hydrochloric acid and water, dried by magnesium sulfate and concentrated on a rotavapor. The residue was taken up in petroleum ether and was suction-filtered through a bed of dry-column silica gel. The filtrate was evaporated to yield the O-(α-bromoisobutyryl)β(+)fenchol as a yellowish oil (27.6 g) having the following properties: $^1$H NMR (CDCl$_3$), δ 0.9 (s, 3H), 1.1 (d, 6H), 1.1–1.85 (m, 7H) 1.95 (s, 6H, isobutyryl), and 4.2 (d, 1H, methine of fenchyl ester).

EXAMPLE 2

Production of O-(α-Azidoisobutyryl)-β(α)fenchol

A mixture of O-(α-bromoisobutyryl)-β(+)fenchol (27.5 g) and sodium azide (9.0 g) in dimethylformamide (50 ml) was heated between 35° C. abd 45° C. with vigorous stirring for 6 hours. After cooling to room temperature, it was poured into ice water and was extracted by petroleum ether. The organic layer was washed with water and silane, dried by magnesium sulfate and evaporated to yield a colorless oil (21.5 g) of O-(α-azidoisobutyryl)β(+)fenchol having the following properties: $^1$H NMR (CDCl$_3$), δ 0.9 (s, 3H), 1,05–1.1

(d, 6H), 1.1–1.95 (m, 7H), 1.5 (s, 6H, isobutyryl), and 4.25 (d, 1H, methine of fenchyl ester).

EXAMPLE 3

Production of O-(β-Amino-isobutyryl)-β(+)fenchol

To O-(α-azidoisobutyryl)-β(+)fenchol (21.0 g) dissolved in ethanol (150 ml) was added 10% Palladium-charcoal (1.3 g). The fenchol product was hydrogenated in a Parr shaker at 54 psi for 3 hours with two intermittent releases and refills of hydrogen. After removal of catalyst and solvent, the product O-(α-aminoisobutyryl)-β(+)fenchol was obtained as a colorless oil (18 g) having the following properties: $^1$H NMR (CDCl$_3$), 0.85 (s, 3H), 1.05 (s, 3H), 1.1 (s, 3H), 1.1–1.8(m, 7H), 1.4 (s, 6H, isobutyryl), 2.2 (s, 2H, NH$_2$), and 4.15 (d, 1H, methine of fenchyl ester). Mass spec., m/e 240 (M+1), 137 (fenchyl). Optical rotation $[\alpha]_D^{25} = -26.14°$ (C, 0.1374, MeOH).

EXAMPLE 4

Production of O-[(β-Benzyl-N-carbobenzyloxy-L-aspartyl-)aminoisobutyryl]-β(+)fenchol A mixture of β-benzyl-N-carbobenzyloxy-L-aspartic acid (30.4 g), and carbonyldiimidazole (13.7 g) in dichloromethane (100 ml) was stirred at room temperature overnight. To this mixture was added a dichloromethane (50 ml) solution of O-(α-aminoisobutyryl)-β(+)-fenchol (17.5 g) and the resulting solution was allowed to stir vigorously at room temperature for 48 hours. The solvent was changed from dichloromethane to ethyl acetate which was then washed in turn with 1N HCl, water, 1N NaOH, saline and was dried by magnesium sulfate. Evaporation gave a yellowish oil (35.6 g). This crude product was purified via silica gel dry columns (CHCl$_3$ as eluant) and pure product O-[(β-benzyl-N-carbobenzyloxy-L-aspartyl)α-aminoisobutyryl]-β(+)fenchol (16.8 g) was obtained as a colorless gum having the following properties: $^1$H NMR (CDCl$_3$), 0.85 (s, 3H), 1.0 (s, 3H), 1.1 (s, 3H), 1.1–1.8 (m, 7H), 1.55 (d, 6H, isobutyryl), 2.7 (dd, 1H), 3.1 (d, 1H), 4.2 (dd, 1H, methine of fenchyl ester), 4.55 (broad s, 1H), 5.1 (d, 4H), 5.9 (broad s, 1H), 7.35 (dd, 10H).

EXAMPLE 5

Production of O-[(β-Benzyl-N-carbobenzyloxy-L-aspartyl)-α-amino-isobutyryl]-β(+)fenchol To a cold solution of β-benzyl-N-carbobenzyloxy-L-aspartic acid (6.4 g) in dichloromethane (100 ml) was added hydroxybenzotriazole hydrate (2.5 g) and dicyclohexylcarbodiimide (3.7 g) with vigorous stirring. After two hours, the insoluble materials were filtered off and the filtrate was evaporated to yield a yellowish oil (14 g). Purification via a silica gel dry column (CHCl$_3$ as eluant) gave pure product as a colorless gum (10.5 g) having the following properties: $^1$H NMR (CDCl$_3$) 0.85 (s, 3H), 1.0 (s, 3H), 1.1 (s, 3H), 1.1–1.8 (m, 7H), 1.55 (d, 6H, isobutyryl), 2.7 (dd, 1H), 3.1 (d, 1H), 4.2 (d, 1H, methine of fenchyl ester), 4.55 (broad s, 1H), 5.1 (d, 4H), 5.9 (broad s, 1H) and 7.35 (dd, 10H).

EXAMPLE 6

Production of N-L-aspartyl methylalanine[β(+)fenchyl]ester

O-[(β-benzyl-N-carbobenzyloxy-L-aspartyl)-α-aminoisobutyryl]-β(+)fenchol (16.8 g) dissolved in methanol (800 ml), containing with 1.5 g of 10% palladium-charcoal, was hydrogenated at 51 psi for 3 hours. After removal of catalyst and solvent, a white solid (8.6 g) of N-L-aspartyl methylalanine[β(+)fenchyl]ester was obtained, m.p. 163°–165° C. (MeOH—H$_2$O). $^1$H NMR (CDCl$_3$+CD$_3$OD) δ 0.9 (d, 3H), 1.05 (d, 6H), 1.1–1.8 (m, 7H), 1.55 (d, 6H), 2.45–2.6 (dd, 1H), 2.65–2.75 (dd, 1H), 3.95 (dd, 1H), and 4.15 (d, 1H). Optical rotation: $[\alpha]_D^{25} = -8.83°$ C. (c, 0.0111, MeOH).

EXAMPLE 7

Production of O-(α-Chloropropanoyl)-α(+)fenchol

A mixture of α(+)-fenchol (10 g), α-chloropropanoyl chloride (8.9 g) and triethylamine (9.8 ml) was stirred in dichloromethane from 0° C. to room temperature overnight. Afterward, it was washed with dilute hydrochloric acid and water, dried by magnesium sulfate and concentrated on a rotavapor. The residue was taken up in petroleum ether and was suction-filtered through a bed of dry-column silica gel. The filtrate was evaporated to yield the product O-(α-chloropropanoyl)-α(+)fenchol as a colorless oil (9.4 g.) having the following properties: $^1$H NMR (CDCL$_3$), δ 0.8 (s, 3H), 1.1 (s, 3H), 1.15 (s, 3H), 1.7 (d, 3H), 1.1–1.8 (m, 7H), 4.45 (s, 1H, fenchyl ester), and 4.5 (q, 1H, alanyl proton).

EXAMPLE 8

Production of O-(α-Azidopropanoyl)-α(+)-fenchol

A mixture of O-(α-chloropropanoyl)-α(+)-fenchol (9.4 g) and sodium azide (3 g) in dimethylformamide (25 ml) is heated between 35° C. and 45° C. with vigorous stirring for 6 hours. After cooling to room temperature, it is poured into ice water and is extracted by petroleum ether. The organic layer is washed with water and saline, dried by magnesium sulfate and evaporated to yield a colorless oil (7 g).

EXAMPLE 9

Production of O-DL-Alanyl-α(+)fenchol

O-(α-Azidopropanoyl)-α(+)fenchol (7 g) dissolved in ethanol (100 ml) containing 10% Palladium-charcoal (0.7 g) was hydrogenated in a Parr shaker at 54 psi for 3 hours with two intermittent releases and refills of hydrogen. After removal of catalyst and solvent, the product is obtained as a colorless oil (6.2 g).

EXAMPLE 10

Production O-[(β-Benzyl-N-carbobenzyloxy-L-aspartyl)-DL-alanyl]-α(+)fenchol

A mixture of β-benzyl-N-carbobenzyloxy-L-aspartic acid (25 g) and carbonyldiimidazole (11.4 g) in dichloromethane (100 ml) was stirred in an ice-bath for 30 minutes. To this mixture was added a dichloromethane (100 ml) solution of O-(DL-alanyl)-α(+)fenchol (16 g) and the resulting solution was allowed to stir vigorously at room temperature for 18 hours. The solvent was changed from dichlormethane to ethyl acetate which was then washed in turn with 1N HCl, water, 1N NaOH, saline and was dried by magnesium sulfate. Evaporation gave a colorless oil (35.5 g). This crude product was purified by a silica gel dry column (20% ethylacetate in hexane as the eluant) and pure product of O-[β-benzyl-N-carbobenzyloxy-L-aspartyl)-DLalanyl]α(+)fenchol (27.4 g) was obtained as a colorless oil.

EXAMPLE 11

Production of N-L-aspartyl-DL-alanine[α(+)fenchyl]ester

O-[(β-Benzyl-N-carbobenzyloxy-L-aspartyl)-DL-alanyl]-α(+)-fenchol (27.4 g) dissolved in ethanol (200 ml) containing 1.2 g of 10% palladium-charcoal, was hydrogenated at 35 psi for 5 hours. The catalyst was filtered off and was washed with methanol. The combined alcohols were evaporated to give N-L-aspartyl-DL-alanine[α(+)-fenchyl]ester as a white solid (14.2 g).

What is claimed is:

1. A compound represented by the formula:

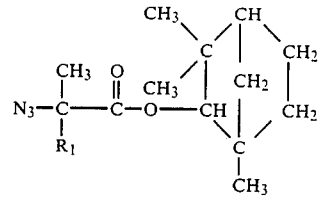

wherein $R_1$ is hydrogen or methyl.

2. The compound of claim 1:
O-(α-Azidoisobutyryl)β(+)fenchol.
3. The compound of claim 1:
O-(α-Azidoisobutyryl)β(−)fenchol.
4. The compound of claim 1:
O-(α-Azidoisobutyryl)α(+)fenchol.
5. The compound of claim 1:
O-(α-Azidoisbutyryl)α(−)fenchol.
6. The compound of claim 1:
O-(α-Azidopropanoyl)α(+)fenchol.
7. The compound of claim 1:
O-(α-Azidopropanoyl)β(−)fenchol.
8. The compound of claim 1:
O-(α-Azidopropanoyl)α(+)fenchol.
9. The compound of claim 1:
O-(α-Azidopropanoyl)α(−)fenchol.

* * * * *